United States Patent [19]

Fontaine

[11] 4,193,992

[45] Mar. 18, 1980

[54] PROCESS FOR THE PREPARATION OF DEFIBRINATED AND LYOPHILIZED PLACENTAL CELLS

[75] Inventor: Gérard Fontaine, Clarens, Switzerland

[73] Assignee: Laboratories Cellorgan S.A., Chatel St. Denis, Switzerland

[21] Appl. No.: 862,911

[22] Filed: Dec. 21, 1977

[30] Foreign Application Priority Data

Aug. 16, 1977 [CH] Switzerland ............... 10013/77

[51] Int. Cl.² ........................................... A61K 35/48
[52] U.S. Cl. ........................................ 424/105; 435/1
[58] Field of Search .................... 424/105; 195/1.8, 2, 195/4

[56] References Cited

U.S. PATENT DOCUMENTS

| | | | |
|---|---|---|---|
| 3,980,432 | 9/1976 | Trobisch et al. | 424/105 |
| 4,054,648 | 10/1977 | Nagasuwa et al. | 424/105 |

FOREIGN PATENT DOCUMENTS

| | | | |
|---|---|---|---|
| 1467784 | 1/1969 | Fed. Rep. of Germany | 424/105 |
| 2459915 | 6/1975 | Fed. Rep. of Germany | 424/105 |
| 299060 | 1/1930 | United Kingdom | 424/105 |

OTHER PUBLICATIONS

*Cell*; No. 1, 12/72, pp. 1, 17, 18, 38, 39 & 76.
Verniary et al.; *Cell,* No. 1, 12/72, pp. 19–39.

*Primary Examiner*—Allen J. Robinson
*Attorney, Agent, or Firm*—Cushman, Darby & Cushman

[57] ABSTRACT

Defibrinated and lyophilized placental cells are prepared by taking the foetomaternal placenta of a ewe killed at the end of the fourth month of gestation, breaking the placenta into fragments, immediately submerging the fragments in Ringer's solution to wash away traces of blood, finely dividing the fragments, placing them in 5% aqueous trypsinated solution, permitting tryptic digestion with stirring, separating the placental cells by filtering, washing the cells in refrigerated Hanks solution, centrifuging in a low temperature centrifuge, suspending the base obtained in the centrifuging step in a minimum of survival liquid and lyophilizing the suspension until constant weight is obtained. The cells obtained are used in the external treatment of ulcers and first and second degree burns.

9 Claims, No Drawings

PROCESS FOR THE PREPARATION OF DEFIBRINATED AND LYOPHILIZED PLACENTAL CELLS

SUMMARY OF THE INVENTION

The present invention relates to a process for the preparation of defibrinated and lyophilized placental cells from the foetomaternal placenta of ewes, the thus obtained cells and their use in medicaments for external use.

The obtaining of cells or placental cell extracts is known, said cells or extracts being used in medicine and/or in cosmetic products.

However, there has now been developed over a relatively long period an optimum process for the preparation of lyophilized placental cells and a novel product obtained by such process.

An object of the invention is a process for the preparation of defibrinated and lyophilized placental cells, wherein the foetomaternal placental of a ewe killed at the end of the fourth month of gestation is broken into fragments, the fragments obtained are immediately submerged in Ringer's solution in order to wash away traces of blood, the fragments are finely divided and placed in a 5% aqueous trypsinated solution, tryptic digestion is effected accompanied by stirring, the placental cells are separated by filtering, washed in refrigerated Hanks solution, e.g., at 10° to 40° C. and separated by centrifuging in a low temperature centrifuge, e.g., at 10° to 40° C., the base obtained from the centrifuging process is suspended in a minimum of survival liquid and the suspension is lyophilized until a constant weight is obtained.

The invention also relates to the placental cells obtained in this way and the use of said cells in medicaments for external use for the treatment of degeneration phenomena, e.g., external ulcers, such as varicose ulcers, decubitus ulcers and first and second degree burns of mammals, e.g., mice, rabbits, dogs, cats and humans.

The product of the process according to the invention is characterized by the following general properties;

Physical

Organoleptic Characteristics

Odorless powder with a slightly salty taste and a more or less deep chestnut color.
Solubility:
At 20° C.:
  soluble in water: 0.140 g necessitates a minimum of 5 ml of water. Solubilization is slow and necessitates stirring for about 1½ to 2 hours. The solution obtained is brown, opalescent and has in fact the appearance of a very fine suspension. insoluble in: methanol, acetone, carbon tetrachloride, ether and benzene.
At 37° C.:
  solubility in water significantly improved (30 minutes with stirring);
  insoluble in methanol, aceton, carbon tetrachloride and ether;
  very slightly soluble in benzene.
pH:
  Determine the pH on a 1% wt/vol solution of protein.

| Batches | 1 | 2 | 3 | 4 | 5 | 6 | 7 |
|---|---|---|---|---|---|---|---|
| Values | 7.40 | 7.52 | 7.60 | 7.32 | 7.66 | 7.60 | 7.43 |

All the values are below pH 7.7.

Rotary power

It could not be measured in view of the opalescence of the product solutions, even when diluted and purified by trichloroacetic acid.

Resistivity

Determined on 2% solutions in water.

| Batches | 1 | 2 | 3 | 4 | 5 | 6 |
|---|---|---|---|---|---|---|
| Ohms cm²/cm | 253 | 212 | 215 | 277 | 182 | 240 |

Average value: 229.8±33.7.
The values obtained are dispersed.

Spectroscopy

Ultraviolet and Visible

The tests carried out on the various samples revealed an intense absorption in far ultraviolet (200 to 225 nm), which was also very marked between 225 and 280 nm. This is due to the high protein content of the medium:
  all amino acids have a large absorption for $\lambda=220$ nm;
  cystine absrobs at 240 nm;
  tyrosine absorbs at 280 nm;
  purine and pyrimidine bases of nucleoproteins absorb at 260 nm.

Infrared

Although it is a complex medium infrared spectra of the product were prepared after pelleting it in potassium bromide.

Although a detailed interpretation of the spectra obtained was impossible due to the complexity of the substance analyzed, they certainly reveal a significant homogeneity between the treated samples.

Chemical

Water content expressed in grams per 100 grams of substance:
Determination by weighing after placing samples in oven at 104° C. until constant weight.

| Batches | 1 | 2 | 3 | 4 | 5 | 6 |
|---|---|---|---|---|---|---|
| Results | 3.23 | 4.20 | 3.85 | 4.70 | 3.70 | 4.02 |

Average value: 3.95±0.49.
The results are homogeneous.
Total ash expressed in grams per 100 grams of substance.
Sample: 0.5 gram—French Pharmacopoeia method, 9th edition, pages 2–300.

| Batches | 1 | 2 | 3 | 4 | 5 | 6 |
|---|---|---|---|---|---|---|
| Results | 9.85 | 9.00 | 8.69 | 9.90 | 9.50 | 9.25 |

Average value: 9.37±0.48.
The results are homogeneous.

Total nitrogen expressed in grams per 100 grams of substance.

Determination of total nitrogen by Kjeldahl's method.

| Batches | 1 | 2 | 3 | 4 | 5 | 6 |
|---|---|---|---|---|---|---|
| Values N | 9.5 | 10.0 | 10.3 | 10.6 | 10.3 | 10.3 |
| Protein Content P | 59.3 | 62.5 | 64.3 | 66.2 | 62.5 | 62.5 |

Average values: N=10.17±0.38: P=62.88±2.29

The analyzed samples have high protein contents. The values obtained were grouped and reveal a certain homogeneity of the studied lyophilizates in this range.

Non-protein nitrogen expressed in grams per 100 grams of substance.

Nitrogen detemination by Kjeldahl's method after deproteinization of the 20% trichloroacetic acid medium.

| Batches | 1 | 2 | 3 | 4 | 5 | 6 |
|---|---|---|---|---|---|---|
| Values | 3.85 | 3.32 | 4.02 | 3.50 | 3.78 | 4.02 |

Average value: 3.75±0.28.

This nitrogenous fraction represents the peptides, amino acids and other nitrogenous components (urea, creatinine, etc.). The values obtained are relatively well grouped and show a certain richness of the medium in this type of composition.

Zonal Electrophoresis performed on a Beckman apparatus.

The tests performed lead to widely differing results relative to the high protein content of the medium and they could not be interpreted.

Glycogen expressed in grams per 100 grams.
Method of Good, Kramer and Somogyi.
"Techniques de laboratoire" by J. Loiseleur, Vol. 1, Part 2, Masson 1963, page 1363.

| Batches | 1 | 2 | 3 | 4 | 5 | 6 |
|---|---|---|---|---|---|---|
| Results | 0.02 | traces | traces | 0.3 | traces | 0.1 |

Virtual absence of glycogen in the samples analyzed, due to the preparation procedure used for the lyophilizates.

Biological

Sterility

Test carried out in accordance with the French Pharmacopoeia, 9th edition, pages 2-238-243.

The 6 samples were normal from the sterility standpoint.

Pyrogenic Substances

The final tests were carried out in accordance with the French Pharmacopoeia, 9th edition, pages 2-235-238. The administration of 0.5 ml of a lyophilizate solution of 140 mg/5 ml per kg of animal with 1 ml of apyrogenic isotonic solution of sodium chloride into the vein of the ear of the rabbit lead to the death of the animal within a few minutes.

The high toxicity of the medicament by the venous route is due to richness in proteins leading to the shocks which wete responsible for the deaths observed.

Histamine Substances

Biological titration was carried out in accordance with the French Pharmacopoeia, 9th edition, pages 2-244-246.

None of the 6 sample has a contracting activity, even at high concentration ($10^{-3}$ at the most). Sometimes (curve no. 5) there was a late (1 to 2 mn) progressive increase in the tonus of the preparation. It could not be attributed to the histamine because it is not consistant during the same test for the same sample and because it is slow to occur, i.e., it differs from a histamine spasm which occurs immediately the product is injected in the tank.

This modification of the tonus can be attributed to variations in the composition of the survival liquid by high protein-rich doses of lyophilizate. Its mixing by air bubbles is accompanied by the formation of large quantities of foam at the top of the tank.

Abnormal Toxicity Test based on French Pharmacopoeia, 9th edition, pages 2-246.

Experimental Data

2% solution in isotonic NaCl;
injected volume 0.5 ml by the intraperitoneal route;
animals: 5 female mice and 5 male mice;
all the animals must survive and must have no illness symptoms 6 days after the injection.

| Batches | 1 | 2 | 3 | 4 | 5 | 6 | Control |
|---|---|---|---|---|---|---|---|
| Results | normal | normal | normal | normal | normal | normal | normal (0.5 ml of NaCl) |

The 9 samples are normal.
Miscellaneous determinations:
Mineral Elements:
Determination of the Main Elements:
Sodium: expressed in mg/g of substance:
determination by flame spectrophotometry.

| Batches | 1 | 2 | 3 | 4 | 5 | 6 |
|---|---|---|---|---|---|---|
| Values | 36.8 | 32.2 | 33.3 | 40.2 | 22.8 | 28.1 |

Average value: 32.23×6.19.
Potassium: expressed in mg/g of substance:
determination by flame spectrophotometry.

| Batches | 1 | 2 | 3 | 4 | 5 | 6 |
|---|---|---|---|---|---|---|
| Values | 3.4 | 2.8 | 3.6 | 4.1 | 3.2 | 2.8 |

Average value: 3.32±0.50.
Calcium: expressed in mg/g substance:
determination by atomic absorption spectrophotometry.

| Batches | 1 | 2 | 3 | 4 | 5 | 6 |
|---|---|---|---|---|---|---|
| Values | 19.1 | 10.2 | 7.6 | 8.4 | 8.4 | 10.2 |

Average value: 10.65±4.27.

Magnesium: expressed in mg/g of substance:
determination by atomic absorption spectrophotometry.

| Batches | 1 | 2 | 3 | 4 | 5 | 6 |
|---|---|---|---|---|---|---|
| Values | 1.0 | 1.2 | 0.9 | 0.8 | 0.9 | 1.2 |

Average value: 1±0.17.

Zinc: expressed in mg/g of substance:
determination by atomic absorption spectrophotometry.

| Batches | 1 | 2 | 3 | 4 | 5 | 6 |
|---|---|---|---|---|---|---|
| Values | 0.12 | 0.12 | 0.12 | 0.10 | 0.11 | 0.12 |

Average value: 0.12±0.01.

Chlorine: expressed in mg/g of substance:
determination on Technicon autoanalyzer (mercurimetry).

| Batches | 1 | 2 | 3 | 4 | 5 | 6 |
|---|---|---|---|---|---|---|
| Values | 26.7 | 33.2 | 28.0 | 28.7 | 33.2 | 35.0 |

Average value: 30.80±3.41.

Phosphorus: expressed in mg/g of substance:
determination on Technicon autoanalyzer.

| Batches | 1 | 2 | 3 | 4 | 5 | 6 |
|---|---|---|---|---|---|---|
| Values | 4.2 | 4.6 | 3.9 | 4.2 | 3.9 | 3.5 |

Average value: 4.05±0.37.

The research shows a relative homogeneity of the samples with an average high calcium content compared with other elements and a constant zinc content.

Research on Heavy Metals

Performed in accordance with French Pharmacopoeia, 8th edition, pages 1569-1571.

The 0.20 gram samples were treated in accordance with method 4.

Results expressed in ppm.

| Batches | 1 | 2 | 3 | 4 | 5 | 6 |
|---|---|---|---|---|---|---|
| Values | 12 | 8 | 14 | 10 | 7 | 14 |

Average value: 10.8±2.9.

The values obtained for all the samples are below 15 ppm.

Amino Acids

The analyses were performed on the Technicon apparatus:
separation of the amino acids by chromatography on ion exchange resin column;
determination after elution by colorimetry with ninhydrin.

The results are expressed in micromoles/g of powder.

| Sample No. | 1 | 2 | 3 | 4 | 5 | 6 |
|---|---|---|---|---|---|---|
| Aspartic Acid | 45.3 | 8.1 | 38.4 | 6.5 | 9.2 | 28.7 |
| Threonine | 61.2 | 14.7 | 53.5 | 12.7 | 10.8 | 51.3 |
| Serine | 119.2 | 26.8 | 102.3 | 21.3 | 18.3 | 71.8 |
| Glutamic Acid | 111.0 | 24.4 | 93.7 | 36.4 | 24.3 | 59.4 |
| Proline | 0 | 0 | 44.1 | 0 | 0 | 14.0 |
| Glycocoll | 75.0 | 17.7 | 65.7 | 19.0 | 11.7 | 51.0 |
| Alanine | 124.5 | 43.8 | 114.7 | 38.0 | 25.2 | 112.5 |
| Valine | 99.1 | 25.2 | 88.8 | 19.8 | 16.5 | 107.7 |
| Cystine | 12.1 | traces | 0 | 1.2 | traces | 3.8 |
| Methionine | 30.0 | 10.0 | 26.6 | 8.4 | 3.1 | 24.3 |
| Isoleucine | 81.1 | 19.6 | 69.3 | 12.0 | 12.0 | 59.4 |
| Leucine | 148.5 | 54.7 | 125.4 | 38.4 | 27.3 | 90.0 |
| Tyrosine | 58.5 | 28.5 | 53.2 | 24.7 | 14.5 | 39.3 |
| Phenylalanine | 74.2 | 28.0 | 66.2 | 21.9 | 13.7 | 52.0 |
| Lysine | 127.5 | 39.7 | 115.2 | 29.6 | 18.0 | 36.3 |
| Histidine | 31.7 | 8.1 | 29.0 | 5.8 | 4.9 | 30.5 |
| Tryptophane | 20.7 | 9.1 | 18.0 | 8.0 | 5.1 | 16.6 |
| Arginine | 92.7 | 35.0 | not shown | 16.8 | 26.5 | 58.0 |
| Citrulline | 0 | 0 | 0 | 0 | 0 | 0 |
| Carnosine | 0 | 0 | 0 | 0 | 0 | 0 |
| Methylhistidine | 0 | 0 | 0 | 0 | 0 | 0 |
| Total | 1312.2 | 392.2 | 1104.1 | 320.5 | 241.1 | 906.6 |

All the amino acids occur in all the samples, except proline which only exists in samples 3 and 6 and cystine which does not exist in sample 3 and which is found in trace form in samples 2 and 5.

However, although the contents of the various amino acids are not negligible (on average 10%) they vary considerably from one sample to the next. This is certainly due to the preparation process (more or less intense tryptic digestion and subsequent washing).

Vitamins

Thiamine

Determination performed according to "Official method of analysis of the Association of Official Agricultural Chemists," page 657.

Results expressed in mg/g of substance.

| Batches | 1 | 2 | 3 | 4 | 5 | 6 |
|---|---|---|---|---|---|---|
| Values | 0 | traces | traces | 0 | traces | 0 |

Riboflavin

Determination performed according to "Official methods of analysis of the Association of Official Agricultural Chemists," page 659.

| Batches | 1 | 2 | 3 | 4 | 5 | 6 |
|---|---|---|---|---|---|---|
| Values | 0 | traces | 0 | 0 | 0 | traces |

Vitamin C

Determination performed according to "Official method of analysis of the Association of Official Agricultural Chemists," page 661.

| Batches | 1 | 2 | 3 | 4 | 5 | 6 |
|---|---|---|---|---|---|---|
| Values | 0 | traces | 0 | 0 | traces | 0 |

The absence of vitamin factors $B_1$, $B_2$ and C in the samples analyzed, despite their existance in the fresh placenta is certainly connected with the medicament preparation procedure (tryptic digestion, washing, etc.), which causes an almost total elimination of the non-protein hydrosoluble elements.

Enzymes

Determination of the enzymatic activities of transaminases, phosphatase, acids and alkalis, aldolase, creatine and phosphokinase.

Test procedure used taken from "Techniques modernes de laboratoire et exploration fonctionnelle," Vol. I, Lucien Hartmann and "Biochemical Test Combination-- Boehringer". A 0.35% solution was used, this dilution having been found necessary due to the coloring.

Transaminases: TGO and TGP determination in ultraviolet: Hartmann, pages 458–461.

Aldolase (FDP): ultraviolet determination: Hartmann, pages 456–466.

Creatine phosphokinase or CPK: Hartmann, pages 462–464.

Acid phosphatase: Biochemical Test Combination-Boehringer.

Alkaline phosphatase: Biochemical Test Combination-Boehringer.

|  | 1 | 2 | 3 | 4 | 5 | 6 | Average Value |
|---|---|---|---|---|---|---|---|
| TGO | 14 | 12 | 22 | 16 | 22 | 15 | 16.8 ± 4.2 |
| TGP | 1 | 1 | 1 | 2 | 2 | 1 | 1.3 ± 0.5 |
| Aldolase | 0.1 | 0 | 0 | 0.2 | 0.1 | 0 | 0.07 ± 0.08 |
| CPK | 0.2 | 0.1 | 0.3 | 0 | 0.2 | 0.1 | 0.15 ± 0.1 |
| Acid phosphatase | 7 | 4 | 2 | 2 | 8 | 3 | 4.3 ± 2.5 |
| Alkaline phosphatase | 25 | 20 | 20 | 25 | 23 | 25 | 23 ± 2.4 |

Results expressed in mU/ml solution.

The results indicate a by no means negligible emzymatic activity, bearing in mind the concentration of product in the solution. The existence of this activity demonstrates that in the proteins constituting the medicament certain of them have retained their normal biological properties.

Hormones

Oestradiol

The experiments and determination tests were carried out by thin layer chromatography using as a basis the procedure of Wiriot and Henry "Techniques modernes de laboratoire et explorations fonctionnelle," Hartmann, page 596 and 25 ml of 2% solution were treated.

Thin layer chromatography was carried out on silica gel G in the benzene-ethanol system. Development was performed by sulphuric acid-ethanol (vol/vol) atomization, followed by placing in the oven for 10 minutes at 105° C. The Rf is oestradiol 0.30±0.03 (Kurt Randeratte, "Chromatographie sur couches minces," 2nd French edition, page 142).

In all cases a reference sample should be used (commercial oestradiol).

It was possible to reveal the presence of oestradiol in all the samples. Compared with the controls the oestradiol quantity was found to be about 50 μg.

Phenol steroids and gonadotropic hormones: biological evaluation.

The uterotropic action of these groups of hormones is known. It was investigated by the direct subcutaneous administration of product solution, based on the procedure of Henry and Wiriot "Techniques modernes de laboratoire et explorations fonctionnelles," Hartmann, page 627.

Each sample was tested on 10 mice which had not reached puberty and with an average weight of 15 grams. The mice had received 0.5 ml of a 1% solution subcutaneously for 3 days. The results are as follows:

| Batches | 1 | 2 | 3 | 4 | 5 | 6 | Control |
|---|---|---|---|---|---|---|---|
| Number of Positive Results Our of 10 Animals Treated | 7 | 8 | 6 | 7 | 9 | 8 | 10 |
| Uterus Weight in mg | 58.54 ± 14.32 | 43.63 ± 20.83 | 38.68 ± 10.17 | 42.50 ± 15.65 | 39.10 ± 16.2 | 50.15 ± 16.40 | 15.77 ± 2.15 |

The test was positive for each batch (doubling of the uterus weight) and consequently revealed the sought uterotropic activity.

Microscopic Examination of the Samples

Procedure thick suspension in physiological solution;
smear preparation on blade;
after drying May-Grunwald-Giemsa staining.

Results:

Batch 1: very rare cellular elements retained, anhistic mass with numerous granular or filamentous elements of a few microns of the ergastoplasmic or microsomial type.

Batch 2: on anhistic base of protein nature numerous granular elements (approx. $0.5\mu$) and short filaments (2 to $3\mu$) resulting from the disintegration of the chromatin of the nuclei. A relatively large number of ovoid or spheroid nuclei are detached on the smear preparation base, their chromatin structure being distintegrated to a greater or lesser extent, but often present in the form of a dense network. Mononuclear or polynuclear blood cells appear in places in a perfectly preserved state, representing about 1% of the nuclear elements described hereinbefore.

Batch 3: identical to Batch 1.

Batch 4: the anhistic base is traversed by very long cytoplasmic filaments (40 to $50\mu$) which are well preserved and form a weak network in which appear nuclei undergoing lysis and unaltered blood cells (15% of the nuclear elements).

Batch 5: the anhistic base only has rare granular or filamentous formations indicative of low nuclear disintegration, while there are very numerous nuclei, 50% of which are perfectly preserved and surrounded by a cytoplasm with clearly defined limits.

Batch 6: identical to Batch 5.

In summarizing, it can be states that the medium is relatively non-homogeneous from the microscopic standpoint and very few cells are completely preserved. There is a more or less marked cellular disintegration (large in batches 1, 2 and 3 and more discreet in batches 5 and 6) which is doubtless due to the defibrination process. Greater standardization would certainly be desirable.

Thus, the products analyzed mainly consist of homogenate of placental cells, which are particularly rich in protein elements.

Toxicological Report on the Defibrinated Lyophilized Placental Cells

| Animals | |
|---|---|
| Rats: | |
| Control batches T | 20 animals |
| Experimental batch A: lyophilizate, administered subcutaneously every two days (thrice weekly) at a dose of 20 mg/kg, i.e., 10 H.T.D.D. (H.T.D.D.: human therapeutic daily dose: 2 mg/kg, i.e., 140 mg for a 70 kg adult). | 20 animals |
| Experimental batch B: lyophilizate, administered subcutaneously every two days (thrice weekly) at a dose of 100 mg/kg, i.e., 50 H.T.D.D. | 20 animals |
| | 60 animals |
| Rabbits: | |
| Control batches T | 10 animals |
| Experimental batch A | 10 animals |
| Experimental batch B | 10 animals |
| | 30 animals |

The doses administered and the administration frequency are as used for the rats.

Observations

The administration route and human dose rate are those proposed to applicant by Laboratoire Cellorgan. When deciding on the frequency of administration applicant took account of the fact that for human beings a single administration by the intramuscular route of 140 mg of dry product dissolved in 5 ml of isotonic NaCl solution is recommended. This injection would possibly only be repeated after several weeks or even months.

The dose rates adopted correspond to those recommended from the medium-term toxicological standpoint:
1 average dose:batches A:10 H.T.D.D.
1 strong dose:batches B:50 H.T.D.D.

Accommodation

The rabbits are placed in individual cages, while 5 rats are placed in each cage, according to batches and sexes.

They are regularly placed in metabolism cages in order to check the urine and feces.

Finally, they are acclimatized for 8 days prior to the experiment and fed with U.A.R. complete feeds.

Examinations Performed

Reaction of the Animals control of growth by weighing the animals individually twice weekly;

clinical manifestations: checking the general state, activity and possibly mortality, as well as the feces and urine;

at the end of the experiment the animals were killed followed by an autopsy.

Weight of the Organs the following organs were removed: adrenal cortex, liver, spleen, kidney, heart, testicles or ovaries.

Histological examinations performed on 50% of the animals. Organs examined: stomach, ilium, liver, kidney, spleen, heart, suprarenals, thyroid gland, testicle or ovary. The test procedure involved fixing the organs with 10% formol, inclusion and section in paraffin and Lillie and Pasternak staining at pH 4.

Examination of the Blood

Blood count and white blood count performed on all the animals;

blood samples taken from the tail (rat) or ear (rabbit) by means of a Potain pipette using Marcano dilution liquid:

numbering the figured blood elements in the hematimetric chamber of N. Fiessinger;

staining the smear preparation by the May-Grunwald-Giemsa method;

hematocrit (rabbits).

Biochemical examinations were performed on an average 50% of the rats and almost all the rabbits.

General Biochemical Balance (a)
various blood constants;
Total cholesterol:
 Liebermann reaction
 Technicon auto-analyzer.
Urea:
 diacetyl monoxime staining reactiom
 Technicon auto-analyzer.
Glycemia:
 potassium ferricyanide reduction
 Technicon auto-analyzer.
Total proteins:
 biuret staining reaction
 Technicon auto-analyzer.
Albumins:
 staining reaction by quantitative fixation of H.A.B.A.
 Technicon auto-analyzer.
Creatinine:
 staining reaction with picric acid in a sodium medium
 Technicon auto-analyzer.
Uric acid:
 staining reaction by reducing a phosphotungstic complex in a phosphotunstous complex
 Technicon auto-analyzer.
Total bilirubin:
 azobilirubin formation
 Technicon auto-analyzer.
Plasma chlorine (rabbits):
 mercurimetric determination
 Technicon auto-analyzer.
Sodium and potassium (rabbits):
 flame spectrophotometry.
(b)
Hepatic balance:
 Serous transaminases: S.G.O.T., S.G.P.T.
 "Techniques modernes de laboratoire et explorations fonctionnelles," page 492.
 Results expressed in colorimetric units.
Alkaline phosphatase:
 paranitrophenyl phosphate method: "Biochemical Test Combination," resulted expressed in mU/ml.
Hepatic glycogen:
 procedure of Good, Kramer and Somogyi.
 "Techniques de laboratoire" by J. Loiseleur, Vol. 1, part 2, Masson 1963, page 1363.
Urine balance:
 carried out successively on the animals during the experiment;

investigation of the main abnormal elements; albumin, glucose, blood and ketone bodies.

The biochemical blood examinations and glycogen determination were performed at the end of the experiment on killing the animals.

Blood was sampled by cardiopuncture.

Conclusions

The lyophilized defibrinated placental cells analyzed constitute a relatively homogeneous system represented essentially by a homogenate of protein-rich (60%), lyophilized placental cells.

The revelation of hormone factors (phenol steroids and gonadotropic hormones) can be considered as a characteristic of the placental nature of the medicament.

Finally, the samples are correct bacteriologically, from the histamine substance standpoint and with respect to the abnormal toxicity test.

Acute Toxicology Examinations on the Lyophilized Defibrinated Placental Cells It is generally accepted that the acute toxicity of a produce must be assessed on two distinct species of animals. In the present case applicant chose mice and rabbits.

The indicated human dose is 100 to 120 mg in a single injection, i.e., approximately 2 mg/kg. Therefore, the H.T.D.D. is 2 mg/kg.

Mice

Due to the limited weight of the mouse it was possible to assess the acute toxicity of the product by the intramuscular injection of 2.5 g/kg, i.e., 1250 H.T.D.D. Eight ampoules each containing 250 mg of Cellorgan placenta D were emptied into a sterile container to which was added physiological solution to give a total volume of 40 ml. 1 ml contains 50 mg of placenta D.

25 mice were distributed into 5 batches each of 5 mice of the same sex and age. The average weight per batch was established prior to injection, on day 10 and on day 20 following the injection. 10 controls received no injection and were distributed into 2 batches each of 5 mice and were weighed on the same dates as the experimental animals.

The experimental animals were weighed individually and each received a single intramuscular injection of 2500 mg/kg of placenta D. For example, a mouse weighing 32 g received 1.6 ml (0.8 ml in each thigh), i.e., 80 mg of placenta D, corresponding to 2.5 g/kg.

Throughout the period od the experiment there was no case of mortality either in the treated mice or in the controls. Two treated mice died accidentally after the deadline fixed for the end of the experiment, i.e., more than 20 days after the date of the injections. Results:
Average Weight of the Mice:

|  | Before Injection | Day 10 | Day 20 |
| --- | --- | --- | --- |
| Batch 1 | 32 | 33.4 | 32 |
| Batch 2 | 30 | 30.6 | 28.4 |
| Batch 3 | 28.5 | 29.8 | 29.4 |
| Batch 4 | 30 | 32.8 | 32 |
| Batch 5 | 32 | 33.8 | 33 |
| Average Value | 30.5 | 32.1 | 30.2 |
| Control Batch 1 | 29 | 30 | 31.5 |
| Control Batch 2 | 29.5 | 30.5 | 32 |

It should be noted that the average weight of the experimental animals increased by 4.2% 10 days after the injection and dropped to the initial level on day 20. However, the average weight of the controls remained virtually stationary.

Rabbits

Due to the greater weight of the rabbit it was not possible to use such high doses as had been used with the mice. The dose used was reduced to 60 H.T.D.D., i.e., 120 mg/kg.

A total weight of 4 grams of placenta D was poured into a sterile container, to which was added physiological solution *) to give a final weight of 40 ml. 1 ml contains 100 mg of placenta D.

*) solutio Ringeri

Twelve adult rabbits were used. Three controls received no injection. The nine experimental rabbits received in each case 120 mg/kg of placenta D by the intramuscular route. All the rabbits were weighed empty before the injection, on day 7, day 14 and day 21. Results:

|  | Before Injection | Day 7 | Day 14 | Day 21 |
| --- | --- | --- | --- | --- |
| Rabbit 1 | 2,400 | 2,450 | 2,700 | 2,900 |
| Rabbit 2 | 2,200 | 2,200 | 2,300 | 2,550 |
| Rabbit 3 | 2,000 | 2,200 | 2,450 | 2,900 |
| Rabbit 4 | 2,200 | 2,350 | 2,300 | 2,550 |
| Rabbit 5 | 2,400 | 2,450 | 2,600 | 2,750 |
| Rabbit 6 | 2,400 | 2,550 | 2,600 | 2,800 |
| Rabbit 7 | 1,800 | 2,000 | 2,100 | 2,300 |
| Rabbit 8 | 3,000 | 3,200 | 3,100 | 2,950 |
| Rabbit 9 | 3,000 | 3,300 | 3,350 | 3,570 |
| Average Value | 2,377 | 2,522 | 2,611 | 2,808 |
| Control Rabbit 1 | 2,400 | 2,450 | 2,600 | 2,700 |
| Control Rabbit 2 | 2,300 | 2,450 | 2,600 | 2,700 |
| Control Rabbit 3 | 2,300 | 2,420 | 2,560 | 2,650 |
| Average Value | 2,333 | 2,423 | 2,570 | 2,670 |

The injected rabbits revealed no abnormal local reaction. The average weight of the rabbits increased regularly, both in the case of the experimental rabbits and in the case of the controls. One rabbit, No. 8, suffered a slight loss of weight due to an attack of coccidiosis.

Conclusions

The results of the experiments carried out on mice and rats revealed no toxicity of the product under investigation.

Teratological Tests on Lyophilized Defibrinated Placental Cells

White mice, distributed into four groups, were used for defibrinated placenta injection experiments. They were chosen from contemporary broods so that they would have roughly the same weight.

1st group: controls

2nd group: injected with 1 g/kg after 8 days of gestation.

3rd group: injected with 1 g/kg after 11 days of gestation.

4th group: injected with 1 g/kg after 14 days of gestation.

In the case of the injected mice no inflammation occurred at the injection point, which generally causes a temporary stress which does not affect the life of the animal.

The gestation period was the same for the injected mice and the controls, i.e., approximately 20¼ days. The control mice gave birth to a total of 84 mice with an average weight of 1.67 g.

The injected mice gave:

a—8 days: 25 mice with an average weight of 1.57 g.
b—11 days: 35 mice with an average weight of 1.60 g.
c—14 days: 34 mice with an average weight of 1.54 g.

There was no case of abortion among the treated mice.

A statistical study revealed that the weight differences at birth are not significant.

The weight increase was regular. The injected mice suffered from no disorders and their progeny was monitored for 6 weeks. The following results were obtained:

Controls: average weight 27.56 g.
8 days: average weight 27.81 g.
11 days: average weight 28.32 g.
14 days: average weight 33.32 g.

The weight differences are not significant.

Observations on the Action of Defibrinated Lyophilized Placental Cells Used as Local Applications to Torpid Cutaneous Lesions Produced in Different Ways and of Which Details Will be Given Hereinafter The placental cells are contained in a medicament in the form of a gel for external use. The dose was administered to all the patients in the form of a daily application below a dressing following washing of the lesion with physiological serum.

Most of the patents were elderly. It sometimes proved necessary to add to the local medication by the gel general medications either of an anti-infectious nature or specific to a general deficient state. These adjuvants are indicated relative to each observation.

The observations are summarized in the following two tables:

Summary Report 24 our of the 26 observations could be used. In the case of 8 gel treatment was only performed for 3 days, the patient complaining of painful tingling after application. The patient made the same complaint following the application of another topical agent. It can be assumed that it was a subjective rather than objective reaction on the part of the patient. The other observation eliminated (No. 19) relates to a patient who refused treatment after two applications, complaining of "local tingling".

Tolerance was perfect in the case of all other patients. The results are broken down as a function of the patient's age below:

|  | Over 80 | 70–80 | 60–70 | 50–60 | Under 50 |
|---|---|---|---|---|---|
| Varicose ulcers, spontaneous | 1 | 2 | 1 | 2 | 1 |
| After traumatism |  | 1 | 5 | 1 | 1 |
| After exersis of malignant tumor |  | 2 |  |  |  |
| Decubitus ulcers | 4 | 1 |  |  |  |
| Burns |  |  |  | 1 | 1 |

The spontaneous occurring ulcers were encountered in all age ranges.

Post-traumatic ulcers frequently occur between the age of 60 and 70. The 2 observations relative to ulcers which occurred on scars following the exersis of a malignant tumor were in the 70 to 80 age group. The decubitus ulcers naturally occur among the older patients.

The age of the patients suffering from burns is not involved in the etiology.

Spontaneous varicose ulcers: 7 patients, 5 excellent results (observations 1, 3, 13, 22, 24), average age 57 and two average results (observations 4 and 20), average age 80.

Post-traumatic varicose ulcers: 8 patients, 6 excellent results (observations 2, 5, 7, 9, 10, 23), average age 61 and two average results (observations 12, 25), average age 57.

Ulcers following exersis of malignant tumor: two observations (21 and 25), one excellent result (21), age 78, one average result (25), age 77.

Decubitus ulcers: 5 observations, 4 excellent results (observations 14, 15, 16, 18), average age 81 and one average result (17), age 84.

Burns: 2 observations, 1 excellent result (6), age 54 and 1 average result (11), age 62.

Conclusions

The local and general tolerance were perfect in 24 out of 26 patients. The effectiveness of the gel was excellent in 17 cases and average in 7 cases. It was never totally ineffective in patients treated for a sufficient time. Following prolonged use in hospitals and when compared with previous observations it was found that the gel gives excellent results in the local treatment of atonic lesions.

DESCRIPTION OF THE PREFERRED EMBODIMENTS

Example

Preparation of defibrinated lyophilized placental cells. These cells were prepared from the foetomaternal placenta of the ewe.

The flock of ewes was formed 15 years ago for the specific use of the Laboratory. The animals are of the brown-black Jura breed of sheep and reproduced without external additions. The flock is kept at a farm at Treyvaux (Fribourg) and is under constant veterinary supervision. Twice yearly, in the spring and autumn, the flock is given both internal and external anti-parasitic treatment.

The ewes used by the Laboratory were separated towards the end of the fourth month of gestation. A blood sample taken in the period just prior to slaughter enabled laboratory examinations to be carried out. The examinations were performed by Veterinaria (Zurich). In addition, after slaughter cotyledon smears were taken to confirm the absence of myagawanella.

The ewes were slaughtered at the Villeneuve abattoir (Sutter, Vaud), Immediately after death the complete uterus was removed with all the necessary aseptia precautions and was transported to the laboratory in a sealed, sterile container.

In the laboratory the uterus was opened, the foetus eliminated and the foetamaternal placenta collected (400 grams). The fragments collected were immediately submerged in Ringer's solution. After washing several times to eliminate traces of blood the fragments were finally divided by using scissors and placed in a 5% trypsinated aqueous solution. Tryptic digestion was performed at 38° C. accompanied by continuous stirring for roughly 2 hours.

The detached placental cells were extracted by filtering and washed 3 times in refrigerated Hanks medium (1). Centrifuging at 1,000 rpm was performed in a refrigerating centrifuge held at 38° C. The final cellular residue was weighed, suspended in a minimum of survival liquid (2) to permit easy lyophilization. Lyophilization was continued until a constant weight was obtained (3 grams cell). The thus obtained powder constitutes the base product of the gel, which was portioned out into ampoules which were sealed under nitrogen or vacuum and stored at +4° C. for the time necessary for the bacteriological sterility controls and the biochemical controls.

(1)
Hanks Medium
(1) Mother Solution.
Prepare the following solutions separately:

| Solution A | |
| --- | --- |
| NaCl | 320 grams |
| KCl | 16 grams |
| MgSO$_4$ . 7H$_2$O | 8 grams |
| CaCl$_2$ | 5.6 grams |

Successively dissolve the salts in bidistilled water and then fill up with bidistilled water to give 2,000 cc. Filter on an L.3 filter.

| Solution B | |
| --- | --- |
| Na$_2$HPO$_4$ . 12H$_2$O | 6 grams (or Na$_2$HPO$_4$) |
| KH$_2$PO$_4$ | 2.4 grams (2H$_2$0:2.4 g) |
| Glucose | 40 grams |

Fill up with bidistilled water to give 600 cc. Add 400 cc. of 0.1% phenol red solution and filter on an L.3 filter.

Separately place 100 cc of each solution in roundbottomed 250 cc flasks with rubber stoppers and deposit in refrigerator.
(2)
Survival Medium
Weigh into a 500 cc Erlenmeyer flask:

| Ascorbic Acid | 100 mg |
| --- | --- |
| Cysteine | 20 mg |
| Glutamine | 300 mg |
| Casein Hydrolyzate | 1 gram |

Gradually dissolved in approximately 1,000 cc of bidistilled water in a 2,000 cc calibrated flask.

| Add | 100 cc | of Hanks Solution A (white) |
| --- | --- | --- |
| | 100 cc | of Hanks Solution B (red) |
| | 20 cc | of biotin |
| | 2 cc | of vitamin B solution |
| | 2 cc | of folic acid |

Fill up to 2,000 cc with bidistilled water.

Hanks medium (1) is prepared by combining Solution A with Solution B. Thus, this balanced salt solution has the following composition in grams per liter:

| NaCl | 8.00 |
| --- | --- |
| KCl | 0.40 |
| CaCl$_2$ | 0.14 |
| MgSO$_4$ . 7H$_2$O | 0.20 |
| NaHPO$_4$ . 12H$_2$O | 0.12 |
| KH$_2$PO$_4$ | 0.16 |
| NaHCO$_3$ | 0.35 |
| Glucose | 1.00 |

Ringer's solution has the following composition:

| Sodium Chloride | 8.6 grams |
| --- | --- |
| Potassium Chloride | 0.3 gram |
| Calcium Chloride | 0.33 gram |

Water sufficient to make 1000 ml solution.

The process can comprise, consist essentially of or consist of the steps set forth with the materials disclosed.

The product of the invention can be used to treat ulcers.

What is claimed is:

1. A process for the preparation of defibrinated and lyophilized placental cells comprising breaking into fragments the foetomaternal placenta of a ewe killed at about the end of the fourth month of gestation, immediately submerging the fragments in Ringer's solution in order to wash away traces of blood, finely dividing the fragments and placing them in a 1 to 10% aqueous trypsinated solution, effecting tryptic digestion in said solution with the aid of stirring, separating the placental cells by filtering, washing the cells in refrigerated Hanks medium and separating the cells by centrifuging at a low temperature, suspending the cellular residue obtained from the centrifuging process in survival liquid and lyophilizing the suspension until a constant weight is obtained.

2. Defibrinated lyophilized placental cells prepared according to the process of claim 1.

3. Defibrinated, lyophilized placental cells soluble in water to the extent of 0.14 grams in 5 ml at 20° C., a 1% solution of said cells having a pH of about 7.3–7.7, a 2% aqueous solution of the cells having a resistivity of about 229.8±33.7 ohms cm$^2$/cm, said cells having intense absorption within the range of 200 to 225 nm and also marked absorption in the range between 225 and 280 nm, an ash content of 9.37±0.48%, a total nitrogen content of 10.17±0.38%, a non-protein nitrogen content of 3.75±0.28%, a sodium content of 32.23±6.19 mg/g, a potassium content of 3.32±0.50 mg/g, a calcium content of 10.65±mg/g, a magnesium content of 1±0.17 mg/g, a zinc content of 0.12±0.01 mg/g, a chlorine content of 30.80±3.41 mg/g and a phosphorus content of 4.05±0.37 mg/g.

4. Defibrinated, lyophilized placental cells according to claim 3 characterized by the ability to be obtained by breaking into fragments the foetomaternal placenta of a ewe killed at about the end of the fourth month of gestation, immediately submerging the fragments in Ringer's solution in order to wash away traces of blood, finely dividing the fragments and placing them in a 5% aqueous trypsinated solution, effecting tryptic digestion in said solution with the aid of stirring, separating the placental cells by filtering, washing the cells in refrigerated Hanks medium and separating the cells by centrifuging at a low temperature, suspending the base obtained from the centrifuging process in survival liquid and lyophilizing the suspension until a constant weight is obtaines.

5. A process according to claim 1 wherein the amount of survival liquid is the minimum required to permit lyophilization of the suspended base.

6. A process according to claim 1 wherein the fragments are placed in a 5 weight % aqueous trypsinated solution.

7. A process according to claim 1 wherein the washing and centrifuging are carried out at 10° to 40° C.

8. A process according to claim 7 wherein there is employed 5% aqueous trypsinated solution, the tryptic digestion is carried out at 38° C. for 2 hours, the cells are washed 3 times in the refrigerated Hanks medium, centrifuging is carried out at 1,000 rpm and at 38° C.

9. A process according to claim 8 including the further step of portioning out the lyophilized product into ampules sealed under nitrogen or vacuum.

* * * * *